United States Patent
Li et al.

(10) Patent No.: US 10,838,496 B2
(45) Date of Patent: Nov. 17, 2020

(54) HUMAN-MACHINE INTERACTION METHOD BASED ON VISUAL STIMULATION

(71) Applicant: SOUTH CHINA UNIVERSITY OF TECHNOLOGY, Guangzhou (CN)

(72) Inventors: Yuanqing Li, Guangzhou (CN); Jing Xiao, Guangzhou (CN); Jun Qu, Guangzhou (CN)

(73) Assignee: SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 0 days.

(21) Appl. No.: 16/461,576

(22) PCT Filed: Jun. 22, 2018

(86) PCT No.: PCT/CN2018/092392
§ 371 (c)(1),
(2) Date: May 16, 2019

(87) PCT Pub. No.: WO2019/001360
PCT Pub. Date: Jan. 3, 2019

(65) Prior Publication Data
US 2019/0369727 A1      Dec. 5, 2019

(30) Foreign Application Priority Data

Jun. 29, 2017   (CN) .......................... 2017 1 0515731
Jun. 29, 2017   (CN) .......................... 2017 1 0516510
Jun. 29, 2017   (CN) .......................... 2017 1 0517400

(51) Int. Cl.
G06F 3/01       (2006.01)
G06F 3/0481     (2013.01)
G06F 3/0482     (2013.01)

(52) U.S. Cl.
CPC .............. G06F 3/015 (2013.01); G06F 3/013 (2013.01); G06F 3/0482 (2013.01); G06F 3/04815 (2013.01)

(58) Field of Classification Search
None
See application file for complete search history.

(56) References Cited

U.S. PATENT DOCUMENTS 9,445,739 B1        9/2016  Payton et al.
2010/0145214 A1*    6/2010  Guan ................. A61B 5/04842
                                                        600/544

(Continued)

FOREIGN PATENT DOCUMENTS

CN      101515199       8/2009
CN      101968715       2/2011

(Continued)

Primary Examiner — Joseph R Haley
(74) Attorney, Agent, or Firm — JMB Davis Ben-David

(57) ABSTRACT

A human-machine interaction method based on visual stimulations. The method can be applied to multiple new technical fields of display, which comprise but are not limited to the fields of virtual reality (VR), augmented reality (AR), mixed reality (MR), holographic projection and glasses-free 3D. The system consists of three parts: a human body biological collection apparatus, a software client for human-machine interaction and a display terminal. Input ports of the software client are connected to a human body physiological signal collection device (in a wired or wireless manner); a user wears the collection device, and communication ports of the client are respectively connected to communication ports of a display module by means of a multichannel communication module. Firstly, the system is initialized, and then starts to run based on a control method of visual stimulations (an object flicker or distortion). If a target is a text input target, an interface is switched to a text input interface, and texts are inputted by using a physiological (Continued)

signal detection algorithm for a human body. If the target is not a text input target, the type of information is determined by using a detection algorithm of a specific physiological signal and visual stimulation feedback information, so as to complete the interaction. Search and switching can be performed among text input boxes, selection options and multiple directories, and a bottom layer of the directories can be reached, so as to select a target.

13 Claims, 5 Drawing Sheets

(56) References Cited

U.S. PATENT DOCUMENTS

| | | | | |
|---|---|---|---|---|
| 2013/0127708 A1* | 5/2013 | Jung | | A61B 5/0006 |
| | | | | 345/156 |
| 2013/0130799 A1* | 5/2013 | Van Hulle | | G06F 3/01 |
| | | | | 463/36 |
| 2014/0333529 A1* | 11/2014 | Kim | | G06F 3/015 |
| | | | | 345/156 |
| 2019/0377477 A1* | 12/2019 | Haist | | G06F 3/03543 |

FOREIGN PATENT DOCUMENTS

| | | |
|---|---|---|
| CN | 103019382 | 4/2013 |
| CN | 103150023 | 6/2013 |
| CN | 103336581 | 10/2013 |
| CN | 103677264 | 3/2014 |
| CN | 103777752 | 5/2014 |
| CN | 103995583 | 8/2014 |
| CN | 104398325 | 3/2015 |
| CN | 106227354 | 12/2016 |
| CN | 106774847 | 5/2017 |
| CN | 206162388 U | 5/2017 |
| CN | 107272905 | 10/2017 |
| CN | 107291240 | 10/2017 |
| CN | 107340863 | 11/2017 |
| WO | 2013135299 | 9/2013 |

* cited by examiner

HUMAN-MACHINE INTERACTION METHOD BASED ON VISUAL STIMULATION

CROSS-REFERENCE TO RELATED APPLICATIONS

This is the U.S. National Stage of International Patent Application No. PCT/CN2018/092392 filed Jun. 22, 2018, which was published in Chinese under PCT Article 21(2), and which in turn claims the benefit of Chinese Patent Application Nos. 201710515731.3, 201710516510.8, and 201710517400.3 all of which filed on Jun. 29, 2017.

TECHNICAL FIELD

The present invention falls within the field of human-machine interaction, and particularly relates to a human-machine interaction method based on visual stimulation.

BACKGROUND ART

Virtual reality (called VR for short), also referred to as LingJing technique, means an advanced human-machine computer interface having essential features of immersion, interactivity and imagination. In the virtual reality technology, the computer graphics, the emulation technique, the multimedia technology, the artificial intelligence technology, the technology of computer science, the concurrent processing technology and the multi-sensor technology are utilized comprehensively, to simulate functions of the sensory organs of humans such as vision, hearing and the tactile sense, so that people can be immersed in a virtual world generated by a computer and can interact with it in real time by natural means such as languages, gestures. A humanized multi-dimensional information space is created. A user not only can feel, by a virtual reality system, immersive verisimilitude experienced in an objective physical world, but also can break through the limitations of space, time and the other objective limitations, to feel experience that cannot be experienced by his/her own in the real world.

AR is also referred to as augmented reality (called AR for short). It is a new technology seamlessly integrating real world information and virtual world information, which simulates and superposes, by science technologies such as computers, entity information (vision information, sound, taste, tactile sense, etc.) can hardly be experienced within a certain time and space range of the real world. Virtual information is applied to the real world and is sensed by human organs, achieving sensual experiences beyond the reality. In simple terms, VR is a fully virtual world, and AR is half-real and half-virtual world.

MR is also referred to as mixed reality (called MR for short) comprises augmented reality and augmented virtuality, and refers to a new visual environment produced by merging the reality world and a virtual world. In the new visual environment, physical objects and digital objects coexist, and interact in real time.

The holographic projection technology is also referred to as a virtual imaging technology, and is a technology recording and reproducing three-dimensional images with the principles of interference and diffraction. The holographic projection technology not only can produce a stereo overhead phantom, but also can enable the phantom to interact with a performer, to complete a performance together, producing shocking performance effects. The most iconic understanding about holographic projection is "Jarvis" in "Iron Man".

The simplest understanding of glass-free 3D is that the effect of watching a 3D movie with naked eyes is just as the effect of watching a 3D movie using a pair of 3D glasses.

Immersive experience enables existing computer interaction tools such as keyboards, mouses and touchpads difficult to be used. How to develop an interaction means more suitable for VR has become the focus of the industry, and is still in the exploration and study stage.

Currently mainstream interaction means primarily include the following:

I. Sensory Immersion

In sensory immersion, interaction is primarily realized by collecting body movements. The disadvantages is that the equipment is cumbersome (the collection of body movements are generally completed using the multi-camera technique) has complex structures, and many gesture commands need to be memorized. The usage scenes are very limited.

II. Interactive Immersion

Interaction is primarily completed by motion tracking and key control. Generic produces include handles, joy sticks, body feeling guns, steering wheels, etc. Though facilities such as handles can realize efficient control, problems of less keys, having a sole function and so on, especially that it needs to be held by a hand, affecting the immersion. A more appropriate solution should be chosen.

Electrooculogram (EOG) is a bioelectrical signal produced by horizontal motion, vertical motion, rotation or blink of eyeballs.

Electromyogram (EMG) is a bioelectrical signal produced by motions a muscle such as being static, contracting and being excited.

Electroencephalogram (EEG) is the overall reflection of electrophysiological activities of cranial nerve cells on cerebral cortex or the surface of scalp. In the aspect of program applications, people also try to realize a brain-computer interface (BCI) by utilizing electroencephalogram signals, and to achieve some control purpose by means of effective extraction and classification of electroencephalogram signals by utilizing the difference in people's electroencephalogram for different sensations, motions or recognition activities.

SUMMARY OF THE INVENTION

Directed for the deficiency in the art, the present invention proposes a human-machine interaction method based on visual stimulation, and particular technical solutions are as follows:

A human-machine interaction method based on visual stimulation, which human-machine interaction method, as shown in FIG. 1, comprises 3 main parts.

The human-machine interaction method of the present invention comprises the following steps:

Step 1: a software client is provided, wherein input ports of the software client are connected to a human body physiological signal collection device (in a wired or wireless manner), a user wears the collection device, and communication ports of the client are respectively connected to communication ports of a display module by means of a multichannel communication module.

The display module in step 1 comprises but is not limited to virtual reality, augmented reality, mixed reality and the other display modes.

The collection device in step 1 comprises but is not limited to various types of apparatus for collecting and amplifying a human body signal.

The software client in step 1 is primarily responsible for accessing a human body physiological signal, human body signal recognition and an interaction operation with the display module.

The so called human body physiological signal in step 1 comprises but is not limited to an EEG, EOG, and EMG signal, which are referred to as human body physiological signals in collection.

Step 2: parameters are configured for a program in the display module, and if there are multiple graphic user interfaces (GUIs) in reality, then an ID number of a currently displayed GUI is passed back to a client program, so as to provide a reference for signal recognition at the client. and options for generating different functions at the GUI interface are provided to a user for choosing, wherein each option corresponds to one virtual object or button, and the user completes a corresponding operation by selecting a needed virtual object or button (for example, typing some character, or implementing some menu function).

Step 3: before a system starts to run, a training operation is performed at first, wherein the user gazes at a flickering target in a training interface (one button is generally used during training); a corresponding operation (blink is required for EOG, a finger movement is required for EMG, and gazing at a target is required for P300 in EEG) is performed while the target is flickering, wherein the above-mentioned collection device synchronously collects a human body bioelectrical signal, performs band-pass filtering on the collected human body bioelectrical signal, truncates a time period length of sampling points (generally 0-600 ms) from data, and performs down-sampling on the sampling points, the down-sampled data constructs a feature vector, and a computer stores a corresponding feature vector each time a virtual key flickers; and a result obtained by averaging the feature vector is used as a threshold, to establish a training model for the user, and make preparation for a later recognition operation.

Step 4: the client completes the recognition and identification of a target button (for example, changing the recognized button to red), and transfers a result to the display module. The display module detects whether an option corresponding to the target (a virtual object or button) is a subdirectory, if yes, then the subdirectory is entered, an interaction interface is updated to an interaction interface of the subdirectory, and processing is performed according to step 2.

Otherwise, a next step is entered.

Step 5: whether the option is a text input type is judged, if it is a text input type, then a next step is entered, otherwise, step 6 is entered.

Step 6: the interaction interface is switched to a text input interface, wherein selection characters in the text input interface are all virtual keys, and after the user's character input is complete, a corresponding function is executed according to an input instruction.

Step 7: a function of the option is executed.

Further, the step 2 comprises the following steps:

Step 21: different options are generated in the GUI, each option corresponding one virtual object or button.

Step 22: the user gazes at a virtual object or button corresponding to an option needing to be selected.

Step 23: each virtual object or button flickers once in a certain sequence or randomly, when the virtual object or button needing to be selected by the user flickers, the target is determined with the operations in step 3: the above-mentioned collection device synchronously collects a human body physiological signal, performs band-pass filtering on the collected human body physiological signal, truncates a time period length of sampling points (generally 0-600 ms) from data, performs down-sampling on the sampling points and performs a waveform detection operation, if a feature thereof passes the waveform detection, then it is considered that a potential target exists, and transformation is performed with a certain algorithm to construct a feature vector; and a computer stores a corresponding feature vector each time a virtual object or button flickers.

Step 24: the feature vector generated in step 23 is compared to a training mode with a certain algorithm, if a similarity exceeds a threshold, then a decision is a target button, and a serial number of the target button is sent to the display module.

Step 25: the display module executes an operation corresponding to the button of the serial number.

Further, the step 6 comprises the following steps:

Step 51: the human-interface interaction interface is switched to a text input interface, wherein selection characters in the text input interface are all virtual objects or buttons.

Step 52: the user gazes at selection characters to be selected.

Step 53: each virtual object or button flickers once in a certain sequence or randomly, and when the virtual object or button needing to be selected by the user flickers, the target is determined with the operations in step 3. The collection device of claim 1 synchronously collects a human body bioelectrical signal, performs band-pass filtering on the collected human body bioelectrical signal, truncates a time period length of sampling points (generally 0-600 ms) from data, performs down-sampling on the sampling points and performs a waveform detection operation, if a feature thereof passes the waveform detection, then it is considered that a potential target exists, and transformation is performed with a certain algorithm to construct a feature vector; and a computer stores a corresponding feature vector each time a virtual object or button flickers.

Step 54: the feature vector generated in step 23 is compared to a training mode with a certain algorithm, if a similarity exceeds a threshold, then a decision is a target button, and a serial number of the target button is sent to the display module.

Step 55: the display module executes a character corresponding to the button of the serial number, and completes character input.

Step 56: step 51 to step 55 are repeated, until text input is complete.

Step 57: a corresponding function is executed according to an input instruction.

The beneficial effects of the present invention are as follows:

In the first, the limitations of a sole user and a sole function currently existing in the human-machine interaction method in VR, AR, MR and relevant fields are solved, and continuous interaction operations can be performed with the interaction method.

In the second, search and switching can be performed among text input boxes, selection options and multiple directories, and a bottom layer of the directories can be reached, so as to select a target. If a target is a text input target, an interface is switched to a text input interface, and texts are input by using human-body biological signal detection. If the target is not a text input target, then an information type is determined by means of detection information of the human-body biological signal and visual feedback information, and a function represented by the information is determined, so as to complete the interaction.

In addition, with respect to the recognition method in the present invention, two methods i.e., waveform matching and a classifier are used in combination, while ensuring an EMG signal or EOG signal is normally detected, misjudgment of an input signal by a system is eliminated, and the detection rate and the recognition degree are improved. When the present invention is used for a virtual keyboard, selection keys flicker in multiple rows; a finger EMG or EOG signal is judged by operating a virtual key in the row, to determine a target selection key. This matches a keyboard input method of an existing PC machine, and can greatly improve the selection efficiency of functional keys.

DETAILED DESCRIPTION OF EMBODIMENTS

Figure 1:
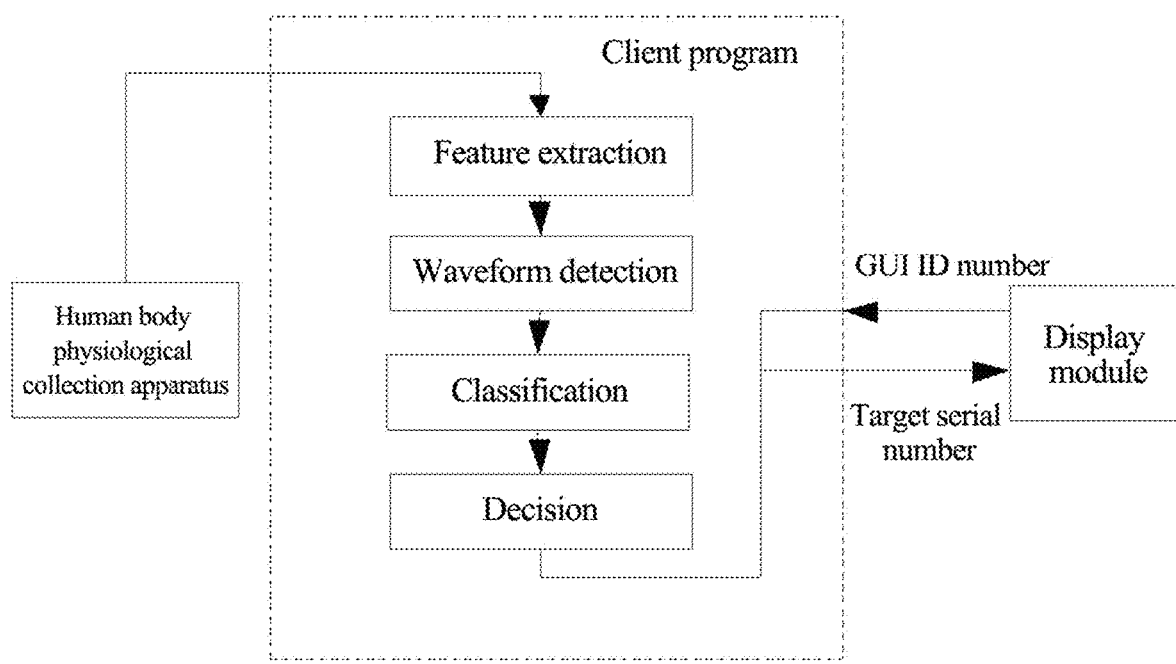
FIG. 1 is a schematic diagram of structural composition of a human-machine interaction system in the present invention.

Preferred embodiments of the present invention will be described below in detail in conjunction with the accompanying drawings such that the advantages and features of the present invention will be easier to understand by a person skilled in the art, so as to define the scope of protection of the present invention more clearly.

Embodiment 1

Particular embodiments of the present invention are as shown in FIGS. 2 to 5, and a virtual reality karaoke bar song choosing system is taken as an example. A virtual reality multi-layer menu interaction method based on a brain-machine interface, wherein the following steps are used in the interaction method:

Step 1: a user wears an electroencephalogram acquisition cap, starts a virtual music song choosing system and enters a brain-machine interaction interface, wherein the virtual music song choosing system consists of four levels of sub-systems.

Step 2: three options, i.e., choosing a song according to singers, choosing a song by pinyin and choosing a song by a song name, are generated in the brain-machine interaction interface, each option corresponding to a P300 virtual key.

Step 3: the user gazes at a P300 virtual key corresponding to an option needing to be selected, wherein it is assumed that the user is gazing at a P300 virtual key correspondingly related to the option of choosing a song by a song name herein.

Step 4: each P300 virtual key flickers once randomly, while the P300 virtual key is flickering, the electroencephalogram acquisition cap synchronously collects a scalp electroencephalogram signal, performs band-pass filtering on the scalp electroencephalogram signal, truncates sampling points of 0-600 ms from electroencephalogram data, and performs 1/6 down-sampling on the above-mentioned sampling points of 0-600 ms, the 1/6 down-sampled data constructs a feature vector, and a computer stores a corresponding feature vector when each P300 virtual key flickers.

Step 5: the above-mentioned step 4 is repeated for 3 times, the computer generates corresponding 3 feature vectors for all the P300 virtual keys, and the 3 feature vectors construct a feature vector set D1.

Step 6: the feature vector set D1 is classified by a classification system, so as to determine a P300 virtual key selected by the user; here, the P300 virtual key corresponds to an option of choosing a song by a song name, in particular, each P300 virtual key super superposes the sum of 3 feature vectors corresponding to 3 turns, and then averages same, for example, the feature vector average of a first P300 virtual key is $D_{average}$:

$$D_{average} = d_1 = \frac{d'_{11} + d'_{12} + d'_{13}}{t}$$

$D_{average}$ is solved for 3 turns of feature vectors corresponding to each P300 virtual key respectively, to obtain a feature vector set $D1=[d_1, d_2, d_3]$, and classification and waveform detection are performed on the feature vector set $D1=[d_1, d_2, d_3]$, to obtain 3 classification results $S=[s_1, s_2, s_3]$ and 3 waveform detection results $W=[w_1, w_2, w_3]$, wherein only first 2 maximum scores are kept for the classification results S, and the remaining one is set to zero; the classification results S and the waveform detection results W are multiplied, to obtain $R^t$:

$$R^t=[r_1{}^t,r_2{}^t,r_3{}^t]=[s_1 \cdot w_1, s_2 \cdot w_2, s_3 \cdot w_3]$$

$R^t$ is a 3-dimensional row vector containing M none-zero values;

$R^t$ is traversed, if there is no $r_i{}^t>0$, then there is no target output in a current turn, and step 3 is returned to, so as to go on detection; and if there is an $r_i{}^t>0$, then it is a target output.

Step 7: whether an option corresponding to the P300 virtual key is a subdirectory, and here the subdirectory is choosing a song by a song name; if yes, then the subdirectory is entered, and here the subdirectory is turning a page of song names; and a brain-machine interaction interface is updated to a brain-machine interaction interface of turning a page of song names, and processing is performed according to step 3 to step 6;

otherwise, a next step is entered.

Step 8: whether the option is a text input type is judged, and it is choosing a song according to singers and choosing a song by pinyin; if it is choosing a song according to singers or choosing a song by pinyin, then a next step is entered, otherwise, step 16 is entered.

Step 9: the brain-interface interaction interface is switched to a text input interface, wherein selection characters in the text input interface are all P300 virtual keys, and the selection characters include 28 characters in total.

Step 10: the user gazes at selection characters to be selected.

Step 11: each selection character flickers once randomly, while the selection character is flickering, the electroencephalogram acquisition cap synchronously collects a scalp electroencephalogram signal, performs band-pass filtering on the scalp electroencephalogram signal, truncates sampling points of 0-600 ms from electroencephalogram data, and performs 1/6 down-sampling on the above-mentioned sampling points of 0-600 ms (selecting one from every 6 sampling points), the 1/6 down-sampled data constructs a feature vector, and a computer stores a corresponding feature vector when each selection character flickers.

Step 12: the above-mentioned step 11 is repeated for 3 times, the computer generates corresponding 3 feature vectors for all the 28 selection characters.

Step 13: the 3 feature vectors corresponding each selection character of the 28 characters are classified by a classification system respectively, so as to determine a character selected by the user, in particular:

n=3 indicates 3 turns in total, each character superposes the sum of 3 feature vectors corresponding to the 3 turns, and then averages same, for example, the feature vector average of a character is $D_{average}$:

$$D_{average} = d_1 = \frac{d'_{11} + d'_{12} + d'_{12}}{t}$$

$D_{average}$ is solved for 3 turns of feature vectors corresponding to each character of the 28 characters respectively, to obtain a feature vector set $D2=[d_1, d_2, \ldots, d_{28}]$, and classification and waveform detection are performed on the feature vector set $D2=[d_1, d_2, \ldots, d_{28}]$, to obtain 28 classification results $S=[s_1, s_2, \ldots, s_i, \ldots, s_{28}]$ and 28 waveform detection results $W=[w_1, w_2, \ldots, w_i, \ldots, w_{28}]$, wherein only first 5 maximum scores are kept for the classification results S, and the remaining are set to zero; the classification results S and the waveform detection results W are multiplied, to obtain $R^t$:

$$R^t=[r_1^t, r_2^t, \ldots, r_i^t \ldots r_{28}^t]=[s_1 \cdot w_1, s_2 \cdot w_2, \ldots, s_i \cdot w_i, \ldots, s_N \cdot w_{28}]$$

$R^t$ is a 28-dimensional row vector containing M none-zero values;

$R^t$ is traversed, if there is no $r_i^t > 0$, then there is no target output in a current turn, and step 10 is returned to, so as to go on detection; and if there is an $r_i^t > 0$, then it is a target output.

Step 14: step 10 to step 13 are chosen repeated, until text input is complete, and here it is the completion of singer name input or the completion of pinyin input.

Step 15: a corresponding function is executed according to an input instruction.

Step 16: a music playing function is executed.

Embodiment II

Figure 2:
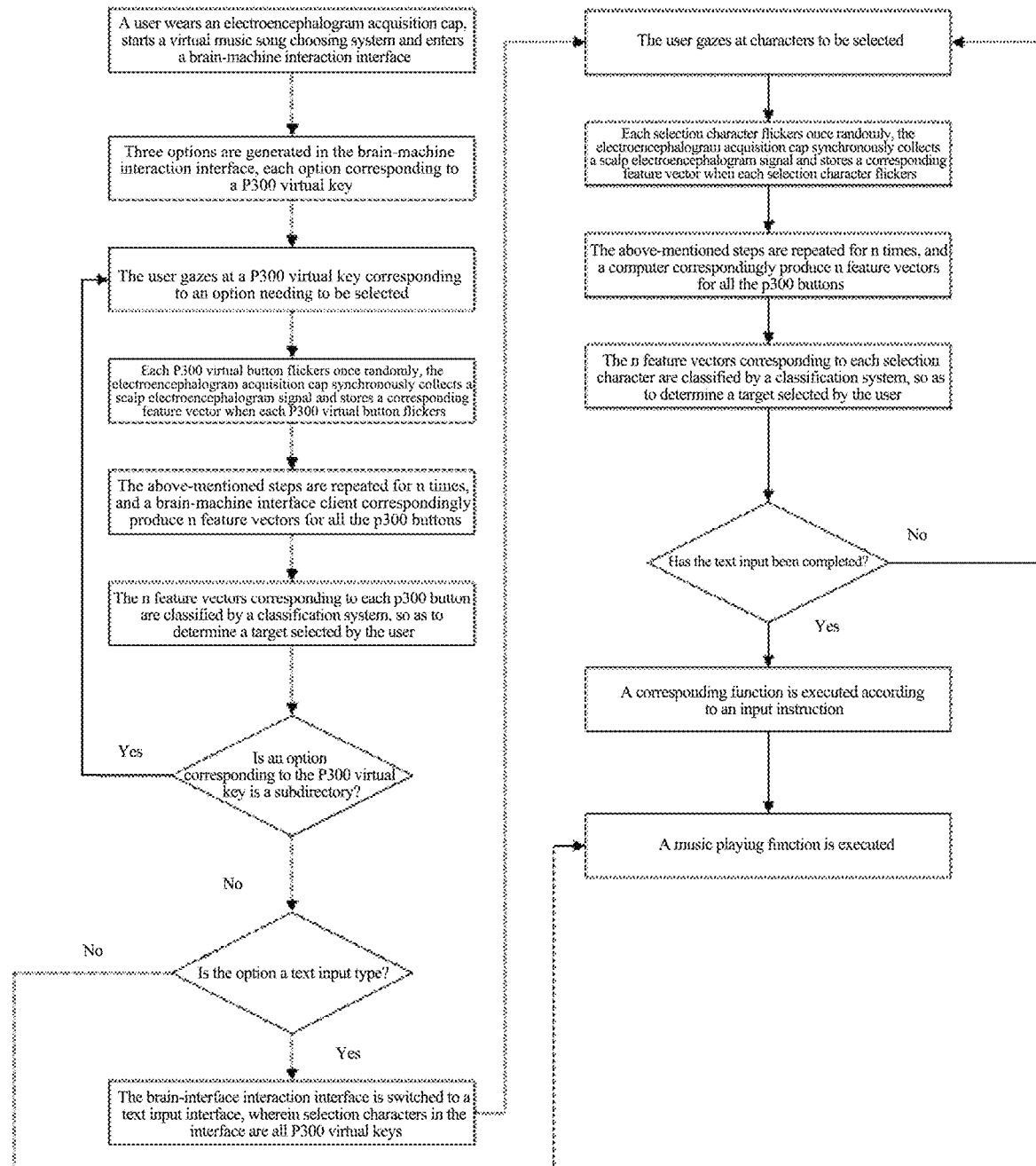
FIG. 2 is a flow chart according to the present invention.
Figure 3:
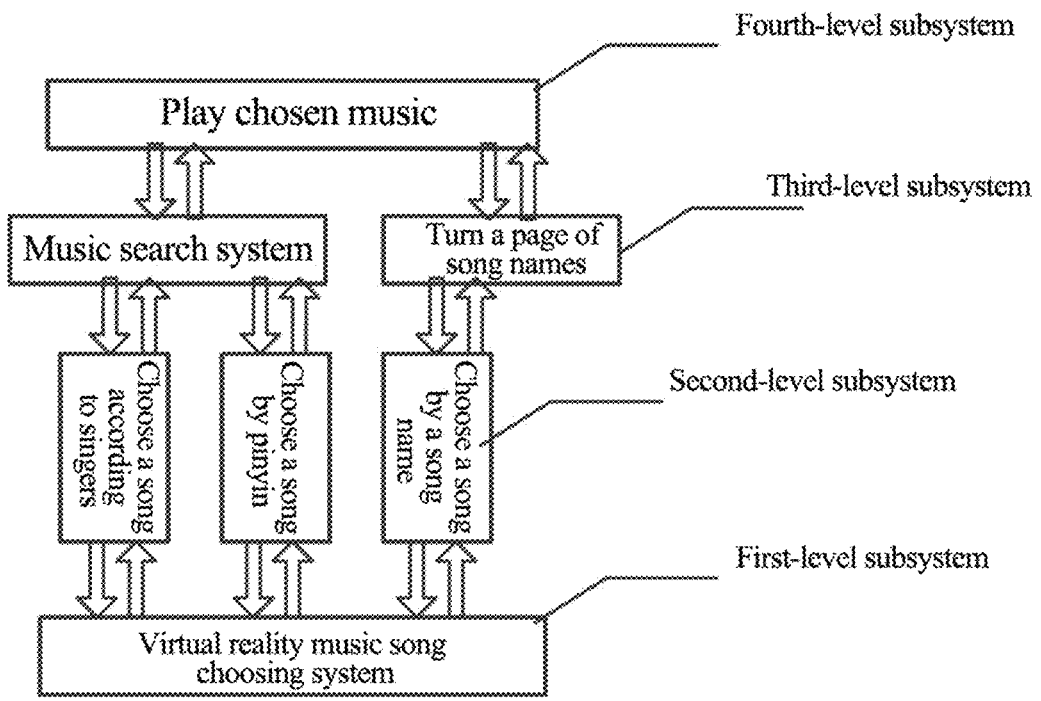
FIG. 3 is a structural diagram of a present virtual karaoke bar song choosing system.
Figure 4:
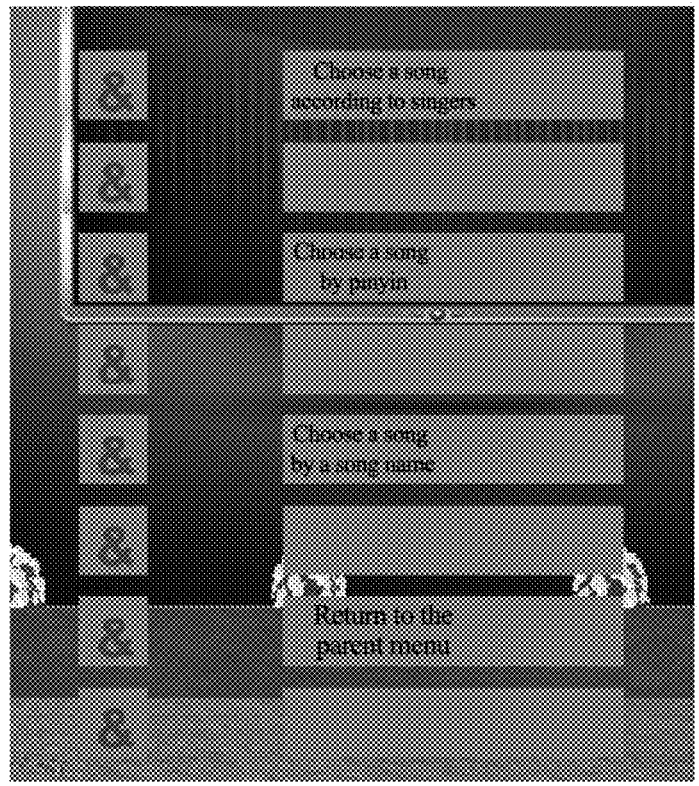
FIG. 4 is a schematic diagram of a brain-machine interaction interface.
Figure 5:
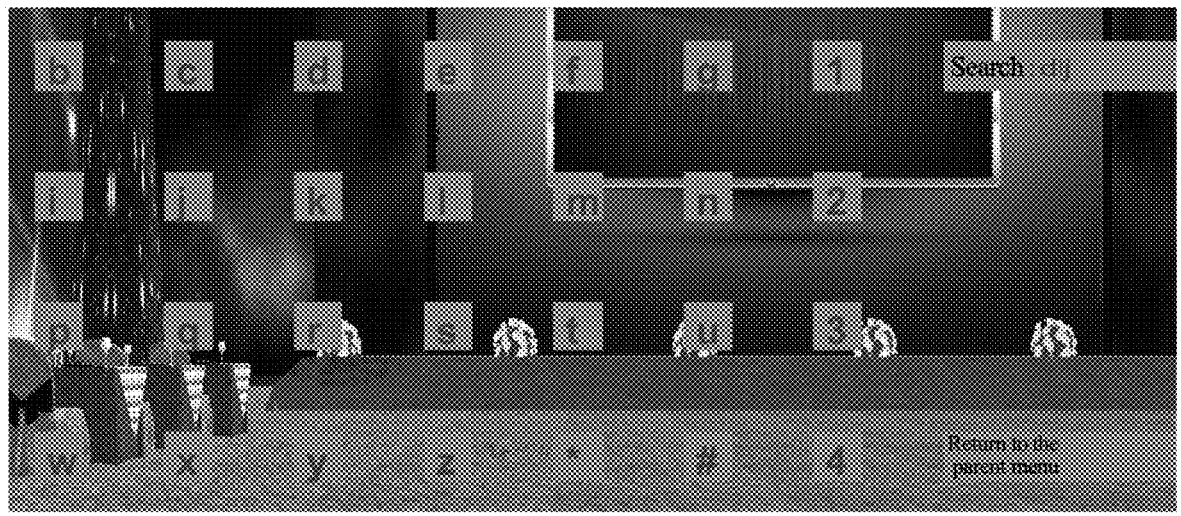
FIG. 5 is a schematic diagram of a text input box.

The embodiment is an interaction method based on EOG and EMG, and the structure of a virtual keyboard is as shown in FIG. 2.

the following steps are used in the method:

Step 1: a user wears an EOG collection apparatus, with a finger EMG collection apparatus being respectively configured on 10 fingers, opens a virtual system and enters a brain-machine interaction interface.

Step 2: 4 selection keys are generated in the brain-machine interaction interface and are represented by numbers 1, 2, 3 and 4 on the virtual keyboard, each selection key corresponds to a row of virtual keys, the row of virtual keys consists of 10 virtual keys, 4 rows and 10 columns of virtual keys are formed in total, the 10 column virtual keys respectively correspond to the 10 finger EMG collection apparatus, the selection of the 4 selection keys is controlled by an EOG signal, and each row of 10 key keys are controlled by a corresponding finger EMG signal, wherein ten keys in each row from the left to right are respectively manipulated by a left-hand little finger EMG, a left-hand ring finger EMG, a left-hand middle finger EMG, a left-hand index finger EMG, a left-hand thumb EMG, a right-hand thumb RMG, a right-hand index finger EMG, a right-hand middle finger EMG, a right-hand ring finger EMG and a right-hand little finger EMG.

Step 3: the 4 selection keys flicker in turn, and only one of the selection keys flickers each time.

Step 4: when a selection key needing to be selected flickers, the user carries out a corresponding eye movement to produce an EOG signal.

Step 5: a computer judges whether there is a selection key being selected, if yes, a row of virtual keys corresponding to the selected selection key is entered, and a next step is entered, otherwise, step 4 is returned to.

Step 6: 10 virtual keys in the row of virtual keys flicker once in turn.

Step 7: when a selection key needing to be selected flickers, the user's finger corresponding to the virtual key makes a corresponding movement to produce a finger EMG signal, when each virtual key flickers, the computer takes a period of signal from the corresponding finger EOG collection apparatus as a feature vector, and the 10 feature vectors form a feature vector set Di.

Step 8: feature vector data in the feature vector set Di is successively preprocessed, including removing baseline drift, removing 50 Hz operating frequency interference, and band-pass filtering.

Step 9: a first-order difference for each pieces of preprocessed vector feature data in the feature vector set Di is solved, and the particular method is: di=xi+1−xi where i denotes an ith sampling point, d denotes a differenced signal, and x denotes a sampling value.

Step 10: for the feature vector set Di=[d1, d2, . . . , dN], the feature vectors in the feature vector set Di respectively correspond to the flicker of n selection keys in an operating row, and the feature vector set Di is classified to obtain n classification results S=[s1, s2, . . . , si, . . . , sN], where only first 5 maximum scores are kept for the classification results S, and the remaining are set to zero.

Step 11: waveform detection is performed on the feature vectors in the feature vector set Di successively.

Step 12: whether a valley appears at a location 30-140 milliseconds later after a peak appears is judged, if yes, a next step is entered, otherwise, step 16 is entered.

Step 13: whether the peak/valley corresponds to a maximum/minimum point of the entire period of signal is judged, if yes, a next step is entered, otherwise, step 16 is entered.

Step 14: whether the total energy of the period of signal from the peak to the valley is greater than a preset threshold P is judged, if yes, then a next step is entered, otherwise, step 16 is entered.

Step 15: if the waveform detection of the feature vector is passed, then corresponding wi=1.

Step 16: if the waveform detection of the feature vector is not passed, then corresponding wi=0.

Step 17: Wi=[w1, w2, . . . , wi, . . . , wN] is obtained.

Step 18: the classification results S and the waveform detection results W are multiplied, to obtain Ri=[r1, r2, . . . , ri, . . . , rN].

Step 19: step 6 and step 18 are circulated for at least one round, to obtain a feature vector set Di+1 and a corresponding Ri+1.

Step 21: whether elements in Ri and Ri+1 are greater than zero is judged, if yes, then a next step is entered, otherwise, step 6 is returned to.

Step 22: whether elements in Ri have the same locations, sequence and size as those in Ri+1 is judged, if yes, a next step is entered, otherwise, step 6 is returned to.

Step 23: if the feature vectors in the feature vector set Di are the same as those in the feature vector set Di+1, a virtual key is determined according to a target feature vector in the feature vector set Di and the feature vector set Di+1.

Step 24: whether a quit button is pressed is judged, if yes, step 28 is entered, otherwise, a next step is entered, wherein the judgment method is particularly: a quit button is configured on the human-machine interaction interface, and the quit button always keep flickering cyclically as the numbers 1, 2, 3 and 4 on the virtual keyboard, and by detecting whether a corresponding EOG signal is produced when the quit button flickers, whether the quit button is pressed is judged.

Step 25: whether input is complete is judged, if input is complete, step 27 is entered, otherwise, a next step is entered, particularly, a confirm button is configured on the human-machine interaction interface, and the confirm button always keep flickering cyclically as the numbers 1, 2, 3 and 4 on the virtual keyboard and as the quit button, and by detecting whether a corresponding EOG signal is produced when the confirm button flickers, whether the quit button is pressed is judged.

Step 26: step 4 to step 22 are repeated.

Step 27: then execution is implemented according to the input virtual key.

Step 28: selection ends.

The particular flow of electrooculogram (EOG) signal detection in step 3 to step 5 mentioned above comprises:

Step 1: the m selection keys flicker in turn, and only one of the selection keys flickers each time.

Step 2: when a selection key needing to be selected flickers, the user carries out a corresponding eye movement to produce an EOG signal, each time the selection key flickers, the EOG collection apparatus takes a period of signal as a feature vector, and m feature vectors compose a feature vector set Mi.

Step 3: feature vector data in the feature vector set Mi is successively preprocessed, including removing baseline drift, removing 50 Hz operating frequency interference, and band-pass filtering.

Step 4: a first-order difference for each pieces of preprocessed vector feature data in the feature vector set Mi is solved, and the particular method is: $di=xi+1-xi$ where i denotes an ith sampling point, d denotes a differenced signal, and x denotes a sampling value.

Step 5: for the feature vector set Mi=[m1, m2, . . . , mm], the feature vectors in the feature vector set Mi respectively correspond to the flicker of m selection keys in an operating row, and the feature vector set Mi is classified to obtain m classification results S=[s1, s2, . . . , si, . . . , sm], where only first q maximum scores are kept for the classification results S, and the remaining are set to zero.

Step 6: waveform detection is performed on the feature vectors in the feature vector set Mi successively.

Step 7: whether a valley appears at a location 30-140 milliseconds later after a peak appears is judged, if yes, a next step is entered, otherwise, step 16 is entered.

Step 8: whether the peak/valley corresponds to a maximum/minimum point of the entire period of signal is judged, if yes, a next step is entered, otherwise, step 16 is entered.

Step 9: whether the total energy of the period of signal from the peak to the valley is greater than a preset threshold P is judged, if yes, then a next step is entered, otherwise, step 16 is entered.

Step 10: if the waveform detection of the feature vector is passed, then corresponding wi=1.

Step 11: if the waveform detection of the feature vector is not passed, then corresponding wi=0.

Step 12: Wi=[w1, w2, . . . , wi, . . . , wm] is obtained.

Step 13: the classification results S and the waveform detection results W are multiplied, to obtain Ri=[r1, r2, . . . , ri, . . . , rN].

Step 14: whether elements in Ri are greater than zero is judged, if yes, then a next step is entered, otherwise, step 2 is returned to.

Step 15: step 6 and step 18 are circulated for at least one round, to obtain a feature vector set Mi+1 and a corresponding Ri+1.

Step 16: whether elements in Ri have the same locations, sequence and size as those in Ri+1 is judged, if yes, a next step is entered, otherwise, step 2 is returned to.

Step 17: a row of virtual keys corresponding to the selected selection key is entered, and the finger EMG apparatus respectively corresponds to the n virtual keys in the row.

Embodiment 3

Figure 6:
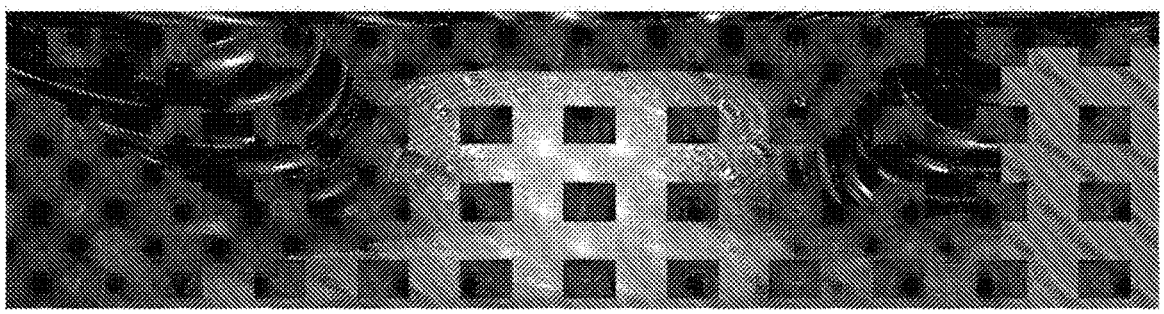
FIG. 6 is a structural diagram of a virtual keyboard.
Figure 7:
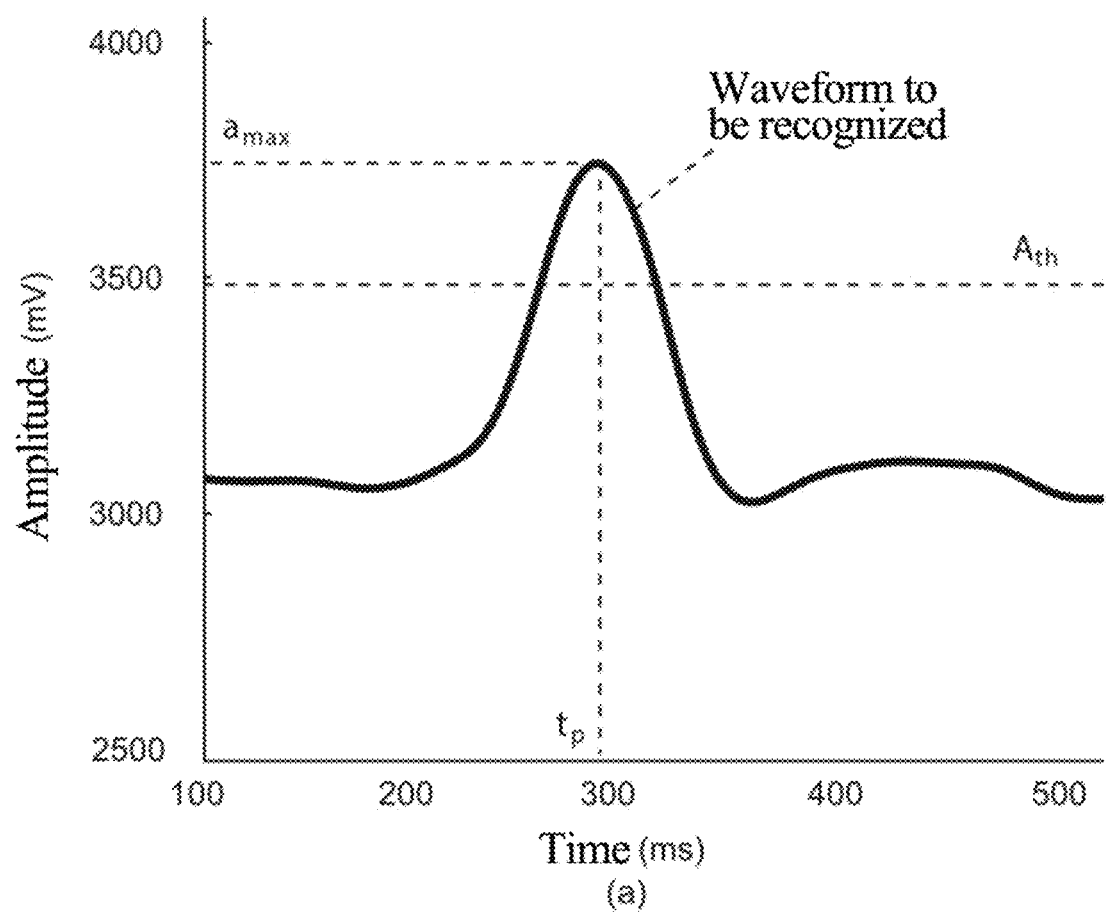
FIG. 7 is a detection oscillogram of an EOG.

This embodiment is an interaction method based on EMG, and particular explanation is made by taking a virtual keyboard as an example in conjunction with FIGS. 2, 6 and 7:

this embodiment is as shown in FIGS. 2, 6 and 7, and the operation of a virtual keyboard is taken as an example.

An interaction method based on EMG, characterized in that the following steps are used:

Step 1: a user connects 10 fingers respectively to 10 signal collection ends of an EMG collection apparatus, opens a virtual system and enters a brain-machine interaction interface.

Step 2: 4 rows of selection keys and 2 rows of buttons are generated in a brain-machine interaction interface, wherein the 2 rows of buttons are respectively a quit row button and a confirm row button, each row of the other 4 rows of selection keys is provided with 10 selection keys, a unique number mark is set for each selection key, and the 10 columns of selection keys in the 4 selection keys respectively correspond to 10 signal collection ends on a one-to-one basis;

ten columns of keys from the left to right are respectively manipulated by a left-hand little finger EMG, a left-hand ring finger EMG, a left-hand middle finger EMG, a left-hand index finger EMG, a left-hand thumb EMG, a right-hand thumb RMG, a right-hand index finger EMG, a right-hand middle finger EMG, a right-hand ring finger EMG and a right-hand little finger EMG;

and one row of the 4 rows of selection keys are selected, then a column of selection keys are selected therefrom, thus a unique number mark can be determined. The quit row button and the confirm row button are also configured with a unique mark; for the quit button, an EMG signal can be input through any one of 10 signal collection ends, here a left-hand index finger EMG is used for signal input; and for the confirm row button, an EMG signal can also be input through any one of 10 signal collection ends, here a right-hand index EMG is used for signal input.

Step 3: the 4 rows of selection keys and the 2 rows of buttons flicker in turn row by row, and when the 4 rows of selection key flicker, an entire row of selection keys simultaneously flicker each time.

Step 4: whether an EMG signal is produced when the entire row flickers is judged, if not, step 3 is returned to, so a next entire row flickers; if yes, then the row is assumed to be an operating row, and step 5 is entered.

Step 5: if the operating row is one of 4 rows of selection keys, the 10 columns of selection keys in the operating row flicker in sequence, when each selection key flickers, a marking system sends a number mark corresponding to the selection key and inserts same to a sampling time axis of the EMG collection apparatus.

Step 6: when a selection key needing to be selected flickers, the user makes a corresponding movement with a finger corresponding to the selection key.

Step 7: the EMG collection apparatus takes a period of signal from the signal collection end corresponding to the number mark as a feature vector, and generates 10 feature vectors when the flickering of the 10 keys are all completed, and the 10 feature vectors form a feature vector set Di.

Step 8: feature vector data in the feature vector set Di is successively preprocessed, including removing baseline drift, removing 50 Hz operating frequency interference, and band-pass filtering.

Step 9: a first-order difference for each pieces of preprocessed vector feature data in the feature vector set Di is solved, and the particular method is:

$di=xi+1-xi$, where i denotes an ith sampling point, d denotes a differenced signal, and x denotes a sampling value.

Step 10: the differenced feature vector set is Di=[d1, d2, . . . , d10], the feature vectors in the feature vector set Di respectively correspond to the flicker of n selection keys in an operating row, and the feature vector set Di is classified to obtain n classification results S=[s1, s2, . . . , si, . . . , s10], where only first 3 maximum scores are kept for the classification results S, and the remaining are set to zero.

Step 11: waveform detection is performed on the feature vectors in the feature vector set Di successively.

Step 12: whether a valley appears at a location 30-140 milliseconds later after a peak appears is judged, if yes, a next step is entered, otherwise, step 16 is entered.

Step 13: whether the peak/valley corresponds to a maximum/minimum point of the entire period of signal is judged, if yes, a next step is entered, otherwise, step 16 is entered.

Step 14: whether the total energy of the period of signal from the peak to the valley is greater than a preset threshold P is judged, if yes, then a next step is entered, otherwise, step 16 is entered.

Step 15: if the waveform detection of the feature vector is passed, then corresponding wi=1.

Step 16: if the waveform detection of the feature vector is not passed, then corresponding wi=0.

Step 17: waveform detection results W=[w1+w2+wi . . . +w10] are obtained by step 15 and step 16, and the classification results S and the waveform detection results W are multiplied, to obtain Ri=[r1, r2, . . . , ri, . . . , r10].

Step 18: Ri is traversed, if there is no ri>0, then determining that there is no target feature vector in the feature vector set Di, and entering step 22, and if there is an ri>0, then determining that there is a target feature vector in the feature vector set Di, and entering a next step.

Step 19: step 5 and step 17 are circulated for at least one round, to obtain a feature vector set Di+1 and a corresponding Ri+1.

Step 20: elements at corresponding locations in Ri and Ri+1 are compared to see whether they are the same, if they are the same, then whether the feature vector set Di and the feature vector set Di+1 contain the same feature vector is judged, a selection key is determined according to the target feature vector in the feature vector set Di and the feature vector set Di+1, the selection of an entire row is quit to, and a next step is entered, otherwise, step 5 is returned to.

Step 21: when the quit row button is in a flickering state, whether the quit row button is pressed is judged, if yes, step 25 is entered, otherwise, a next step is entered.

Step 22: when the confirm row button is in a flickering state, whether the confirm row button is pressed is judged, if yes, step 24 is entered, otherwise, a next step is entered.

Step 23: a next operating row is entered, and step 4 to step 22 are repeated.

Step 24: then execution is implemented according to an input selection option.

Step 25: selection ends.

The invention claimed is:

1. A human-machine interaction method based on visual stimulation, characterized in that the human-machine interaction method comprises the following steps:

step 1: a software client is provided, wherein input ports of the software client are connected to a human body physiological signal collection device in a wired or wireless manner, a user wears the collection device, and communication ports of the client are respectively connected to communication ports of a display module by means of a multichannel communication module;

the display module is used for virtual reality (VR), augmented reality (AR), mixed reality (MR), holographic projection or glass-free 3D;

the collection device is an apparatus for collecting and amplifying a human body signal;

the software client is used for accessing a human body physiological signal, relevant algorithm detection for human body signal recognition and an interaction operation with the display module; and the human body physiological signal is an EEG, EOG, or EMG signal;

step 2: parameters are configured for a program in the display module, and if there are multiple graphic user interfaces (GUIs) in reality, then an ID number of a currently displayed GUI is passed back to a client program, so as to provide a reference for signal recognition at the client; and options for generating different functions at the GUI interface are provided to a user for choosing, wherein each option corresponds to one virtual object or button, and the user completes a corresponding operation by selecting a needed virtual object or button;

step 3: before a system starts to run, a training operation is performed at first, wherein the user gazes at a flickering target in a training interface, for visual stimulation; a corresponding operation is performed while the target is flickering, wherein the collection device synchronously collects a human body bioelectrical signal, performs band-pass filtering on the collected human body bioelectrical signal, truncates a time period length of sampling points from data, and performs down-sampling on the sampling points, the down-sampled data constructs a feature vector, and a computer stores a corresponding feature vector each time a virtual key flickers; and a result obtained by averaging the feature vector is used as a threshold, to establish a training model for the user, and make preparation for a later recognition operation;

step 4: the client completes the recognition and identification of a target button, and transfers a result to the display module; the display module detects whether an option corresponding to the target is a subdirectory, if yes, then the subdirectory is entered, an interaction interface is updated to an interaction interface of the subdirectory, and processing is performed according to step 2;

otherwise, a next step is entered;

step 5: whether the option is a text input type is judged, if it is a text input type, then a next step is entered, otherwise, step 6 is entered;

step 6: the interaction interface is switched to a text input interface, wherein selection characters in the text input interface are all virtual keys, and after the user's character input is complete, a corresponding function is executed according to an input instruction; and step 7: a function of the option is executed;

wherein the step 2 comprises the following steps:

step 21: different options are generated in the GUI, each option corresponding one virtual object or button;

step 22: the user gazes at a virtual object or button corresponding to an option needing to be selected;

step 23: each virtual object or button flickers once in a certain sequence or randomly, when the virtual object or button needing to be selected by the user flickers, the target is determined with the operations in step 3: the collection device synchronously collects a human body physiological signal, performs band-pass filtering on the collected human body physiological signal, truncates a time period length of sampling points from data, performs down-sampling on the sampling points and performs a waveform detection operation, if a feature thereof passes the waveform detection, then it is considered that a potential target exists, and transformation is performed with a certain algorithm to construct a feature vector; and a computer stores a corresponding feature vector each time a virtual object or button flickers;

step 24: the feature vector generated in step 23 is compared to a training mode with a certain algorithm, if a similarity exceeds a threshold, then a decision is a target button, and a serial number of the target button is sent to the display module; and step 25: the display module executes an operation corresponding to the button of the serial number.

2. The human-machine interaction method based on visual stimulation according to claim 1, characterized in that the step 6 comprises the following steps:

step 51: the human-interface interaction interface is switched to a text input interface, wherein selection characters in the text input interface are all virtual objects or buttons;

step 52: the user gazes at selection characters to be selected;

step 53: each virtual object or button flickers once in a certain sequence or randomly, when the virtual object or button needing to be selected by the user flickers, the target is determined with the operations in step 3: the collection device synchronously collects a human body bioelectrical signal, performs band-pass filtering on the collected human body bioelectrical signal, truncates a time period length of sampling points from data, performs down-sampling on the sampling points and performs a waveform detection operation, if a feature thereof passes the waveform detection, then it is considered that a potential target exists, and transformation is performed with a certain algorithm to construct a feature vector; and a computer stores a corresponding feature vector each time a virtual object or button flickers;

step 54: the feature vector generated in step 23 is compared to a training mode with a certain algorithm, if a similarity exceeds a threshold, then a decision is a target button, and a serial number of the target button is sent to the display module;

step 55: the display module executes a character corresponding to the button of the serial number, and completes character input;

step 56: step 51 to step 55 are repeated, until text input is complete; and step 57: a corresponding function is executed according to an input instruction.

3. A virtual reality multi-layer menu interaction method based on a brain-machine interface, characterized in that the following steps are used in the interaction method:

step 1: a user wears an electroencephalogram acquisition cap, starts a virtual reality system and enters a brain-machine interaction interface;

step 2: different options are generated in the brain-machine interaction interface, each option corresponding to a P300 virtual key, and the user selects a needed P300 virtual key;

step 3: whether an option corresponding to the needed P300 virtual key is a subdirectory, if yes, then the subdirectory is entered, a brain-machine interaction interface is updated to a brain-machine interaction interface of the subdirectory, and processing is performed according to step 2; otherwise, a next step is entered;

step 4: whether the option is a text input type is judged, if it is a text input type, then a next step is entered, otherwise, step 6 is entered;

step 5: the brain-machine interaction interface is switched to a text input interface, wherein selection characters in the text input interface are all P300 virtual keys, and after the user's character input is complete, a corresponding function is executed according to an input instruction; and step 6: a function of the option is executed;

wherein the step 2 comprises the following steps:

step 21: different options are generated in the brain-machine interaction interface, each option corresponding to a P300 virtual key;

step 22: the user gazes at a P300 virtual key corresponding to an option needing to be selected;

step 23: each P300 virtual key flickers once randomly, while the P300 virtual key is flickering, the electroencephalogram acquisition cap synchronously collects a scalp electroencephalogram signal, performs band-pass filtering on the scalp electroencephalogram signal, truncates sampling points of 0-600 ms from electroencephalogram data, and performs 1/6 down-sampling on the sampling points of 0-600 ms, the 1/6 down-sampled data constructs a feature vector, and a computer stores a corresponding feature vector when each P300 virtual key flickers;

step 24: the above-mentioned step 22 to step 23 are repeated for n times, the computer generates corresponding N feature vectors for all the P300 virtual keys, and the N feature vectors construct a feature vector set D1; and step 25: the feature vector set D1 is classified by a classification system, so as to determine a P300 virtual key selected by the user.

4. The virtual reality multi-layer menu interaction method based on a brain-machine interface according to claim 3, characterized in that the step 5 comprises the following steps:

step 51: the brain-interface interaction interface is switched to a text input interface, wherein selection characters in the text input interface are all P300 virtual keys;

step 52: the user gazes at selection characters to be selected;

step 53: each selection character flickers once randomly, while the selection character is flickering, the electroencephalogram acquisition cap synchronously collects a scalp electroencephalogram signal, performs band-pass filtering on the scalp electroencephalogram signal, truncates sampling points of 0-600 ms from electroencephalogram data, and performs 1/6 down-sampling on the sampling points of 0-600 ms, the 1/6 down-sampled data constructs a feature vector, and a computer stores a corresponding feature vector when each selection character flickers;

step 54: the above-mentioned step 52 to step 53 are repeated for n times, the computer generates corresponding N feature vectors for all the selection characters, and the N feature vectors construct a feature vector set D2;

step 55: the feature vector set D2 is classified by a classification system, so as to determine a character selected by the user;

step 56: step 52 to step 55 are repeated, until text input is complete; and step 57: a corresponding function is executed according to an input instruction.

5. An interaction method based on EOG and EMG, characterized in that
the following steps are used:

step 1: a user wears an EOG collection apparatus, with a finger EMG collection apparatus being configured on at least n fingers, opens a system and enters a brain-machine interaction interface;

step 2: m selection keys are generated in the brain-machine interaction interface, each selection key corresponds to a row of virtual keys, the row of virtual keys consists of n virtual keys, m rows and n columns of virtual keys are formed in total, the n column virtual keys respectively correspond to the n finger EMG collection apparatus, the selection of the m selection keys is controlled by an EOG signal, and each row of n key keys are controlled by a corresponding finger EMG signal;

step 3: the m selection keys flicker in turn, and only one of the selection keys flickers each time;

step 4: when a selection key needing to be selected flickers, the user carries out a corresponding eye movement to produce an EOG signal;

step 5: a computer judges whether there is a selection key being selected, if yes, a row of virtual keys corresponding to the selected selection key is entered, and a next step is entered, otherwise, step 4 is returned to;

step 6: n virtual keys in the row of virtual keys flicker once in turn;

step 7: when a selection key needing to be selected flickers, the user's finger corresponding to the virtual key makes a corresponding movement to produce a finger EMG signal, when each virtual key flickers, the computer takes a period of signal from the corresponding finger EOG collection apparatus as a feature vector, and the n feature vectors form a feature vector set Di;

step 8: the feature vectors in the feature vector set Di are preprocessed, and the feature vectors are judged by a classifier;

step 9: step 4 to step 8 are circulated for at least one round, to obtain a feature vector set Di+1;

step 10: whether the feature vectors in the feature vector set Di are the same as those in the feature vector set Di+1 is judged, if all of them are the same, a virtual key is determined according to the target feature vectors in the feature vector set Di and the feature vector set Di+1, and a next step is entered, otherwise, step 6 is returned to;

step 11: whether a quit button is pressed is judged, if yes, step 15 is entered, otherwise, a next step is entered;

step 12: whether input is complete is judged, if input is complete, step 14 is entered, otherwise, a next step is entered;

step 13: step 4 to step 12 are repeated;

step 14: then execution is implemented according to the input virtual key; and step 15: selection ends.

6. The interaction method based on EOG and EMG according to claim 5, characterized in that the step 8 comprises the following steps:

step 81: feature vector data in the feature vector set Di is successively preprocessed, including removing baseline drift, removing 50 Hz operating frequency interference, and band-pass filtering;

step 82: a first-order difference for each pieces of preprocessed vector feature data in the feature vector set Di is solved, and the particular method is: $d_i = x_{i+1} - x_i$, where i denotes an ith sampling point, d denotes a differenced signal, and x denotes a sampling value;

step 83: for the feature vector set Di=[d1, d2, ..., dN], the feature vectors in the feature vector set Di respectively correspond to the flicker of n selection keys in an operating row, and the feature vector set Di is classified to obtain n classification results S=[s1, s2, ..., si, ..., sN], where only first q maximum scores are kept for the classification results S, and the remaining are set to zero;

step 84: waveform detection is performed on the feature vectors in the feature vector set Di, to obtain n waveform detection results Wi=[w1, w2, ..., wi, ..., wN]; and step 85: the classification results S and the waveform detection results W are multiplied, to obtain Ri=[r1, r2, ..., ri, ..., rN].

7. The interaction method based on EOG and EMG according to claim 5, characterized in that the step 5 comprises the following steps:

step 91: step 4 and step 7 are circulated for at least one round, to obtain a feature vector set Di+1 and a corresponding Ri+1; and step 92: elements at corresponding locations in Ri and Ri+1 are compared to see whether they are the same, if they are the same, then whether the feature vector set Di and the feature vector set Di+1 contain the same feature vector is judged, a selection key is determined according to the target feature vector in the feature vector set Di and the feature vector set Di+1, and a next step is entered, otherwise, step 4 is returned to.

8. The interaction method based on EOG and EMG according to claim 5, characterized in that the step 84 comprises the following steps:

step 841: waveform detection is performed on the feature vectors in the feature vector set Di successively;

step 842: whether a valley appears at a location 30-140 milliseconds later after a peak appears is judged, if yes, a next step is entered, otherwise, step 846 is entered;

step 843: whether the peak/valley corresponds to a maximum/minimum point of the entire period of signal is judged, if yes, a next step is entered, otherwise, step 846 is entered;

step 844: whether the total energy of the period of signal from the peak to the valley is greater than a preset threshold P is judged, if yes, then a next step is entered, otherwise, step 846 is entered;

step 845: if the waveform detection of the feature vector is passed, then corresponding wi=1;

step 846: if the waveform detection of the feature vector is not passed, then corresponding wi=0; and step 847: Wi=[w1, w2, ..., wi, ..., wN] is obtained.

9. The interaction method based on EOG and EMG according to claim 5, characterized in that the step 10 comprises the following steps:

step 101: whether elements in Ri and Ri+1 are greater than zero is judged, if yes, then a next step is entered, otherwise, step 6 is returned to;

step 102: whether elements in Ri have the same locations, sequence and size as those in Ri+1 is judged, if yes, a next step is entered, otherwise, step 6 is returned to; and step 103: if the feature vectors in the feature vector set Di are the same as those in the feature vector set Di+1, a virtual key is determined according to a target feature vector in the feature vector set Di and the feature vector set Di+1.

10. An interaction method based on EMG, characterized in that the following steps are used:

step 1: a user connects n fingers respectively to n signal collection ends of an EMG collection apparatus, opens a virtual system and enters a brain-machine interaction interface;

step 2: m rows and n columns of selection keys are generated in a brain-machine interaction interface, a unique number mark is set for each selection key, and the n columns of selection keys respectively correspond to n signal collection ends on a one-to-one basis;

step 3: the m rows of selection keys flicker in turn row by row, and an entire row of selection keys simultaneously flicker each time;

step 4: whether an EMG signal is produced when the entire row of selection keys flicker is judged, if not, step 3 is returned to, so a next entire row of selection keys flicker; if yes, then the row is assumed to be an operating row, and step 5 is entered;

step 5: the n columns of selection keys in the operating row flicker in sequence, when each selection key flickers, a marking system sends a number mark corresponding to the selection key and inserts same to a sampling time axis of the EMG collection apparatus;

step 6: when a selection key needing to be selected flickers, the user makes a corresponding movement with a finger corresponding to the selection key;

step 7: the EMG collection apparatus takes a period of signal from the signal collection end corresponding to the number mark as a feature vector, and generates n feature vectors when the flickering of the n keys are all completed, and the n feature vectors form a feature vector set Di;

step 8: the feature vectors in the feature vector set Di are preprocessed, and the feature vectors are judged by a classifier;

step 9: whether a target feature vector exists in the feature vector set Di, if the target feature vector exists, then a next step is entered, otherwise, step 12 is entered;

step 10: step 5 to step 9 are circulated for at least one round, to obtain a feature vector set Di+1, whether the feature vectors in the feature vector set Di are the same as those in the feature vector set Di+1 is judged, if all of them are the same, a selection key is determined according to the target feature vectors in the feature vector set Di and the feature vector set Di+1, and a next step is entered, otherwise, step 5 is returned to;

step 11: whether the selection key indicates to end output is judged, if yes, step 15 is entered, otherwise, a next step is entered;

step 12: whether input is complete is judged, if input is complete, step 14 is entered, otherwise, a next step is entered;

step 13: a next operating row is entered, and processing is executed in the sequence of step 4 to step 12; step 14: then execution is implemented according to an input selection option; and step 15: selection ends.

11. The interaction method based on EMG according to claim 10, characterized in that the step 8 comprises the following steps:

step 81: feature vector data in the feature vector set Di is successively preprocessed, including removing baseline drift, removing 50 Hz operating frequency interference, and band-pass filtering;

step 82: a first-order difference for each pieces of preprocessed vector feature data in the feature vector set Di is solved, and the particular method is: di=xi+1−xi, where i denotes an ith sampling point, d denotes a differenced signal, and x denotes a sampling value;

step 83: for the feature vector set Di=[d1, d2, ..., dN], the feature vectors in the feature vector set Di respectively correspond to the flicker of n selection keys in an operating row, and the feature vector set Di is classified to obtain n classification results S=[s1, s2, ..., si, ..., sN], where only first q maximum scores are kept for the classification results S, and the remaining are set to zero;

step 84: waveform detection is performed on the feature vectors in the feature vector set Di, to obtain n waveform detection results Wi=[w1, w2, ..., wi, ..., wN]; and step 85: the classification results S and the waveform detection results W are multiplied, to obtain Ri=[r1, r2, ..., ri, ..., rN]; and step 9 particularly comprises: traversing Ri, if there is no ri>0, then determining that there is no target feature vector in the feature vector set Di, and entering step 12, and if there is an ri>0, then determining that there is a target feature vector in the feature vector set Di, and entering a next step.

12. The interaction method based on EMG according to claim 10, characterized in that the step 9 comprises the following steps:

step 101: step 5 to step 9 are circulated for at least one round, to obtain a feature vector set Di+1 and a corresponding Ri+1; and step 102: elements at corresponding locations in Ri and Ri+1 are compared to see whether they are the same, if they are the same, then whether the feature vector set Di and the feature vector set Di+1 contain the same feature vector is judged, a selection key is determined according to the target feature vector in the feature vector set Di and the feature vector set Di+1, and a next step is entered, otherwise, step 5 is returned to.

13. The interaction method based on EMG according to claim 10, characterized in that the step 84 comprises the following steps:

step 841: waveform detection is performed on the feature vectors in the feature vector set Di successively;

step 842: whether a valley appears at a location 30-140 milliseconds later after a peak appears is judged, if yes, a next step is entered, otherwise, step 846 is entered;

step 843: whether the peak/valley corresponds to a maximum/minimum point of the entire period of signal is judged, if yes, a next step is entered, otherwise, step 846 is entered;

step 844: whether the total energy of the period of signal from the peak to the valley is greater than a preset threshold P is judged, if yes, then a next step is entered, otherwise, step 846 is entered;

step 845: if the waveform detection of the feature vector is passed, then corresponding wi=1;

step 846: if the waveform detection of the feature vector is not passed, then corresponding wi=0; and step 847: Wi=[w1, w2, . . . , wi, . . . , wN] is obtained.

\* \* \* \* \*